United States Patent
Fiacco et al.

(10) Patent No.: US 10,323,067 B2
(45) Date of Patent: Jun. 18, 2019

(54) METHODS AND COMPOSITIONS FOR CONTROLLING GENE EXPRESSION AND TREATING CANCER

(71) Applicant: EVORX TECHNOLOGIES, INC., Pasadena, CA (US)

(72) Inventors: Stephen V. Fiacco, South Pasadena, CA (US); Amanda N. Hardy, Pasadena, CA (US); Terry T. Takahashi, Pasadena, CA (US)

(73) Assignee: EVORX TECHNOLOGIES, INC., Pasadena, CA (US)

( * ) Notice: Subject to any disclaimer, the term of this patent is extended or adjusted under 35 U.S.C. 154(b) by 0 days.

(21) Appl. No.: 15/310,950

(22) PCT Filed: May 14, 2015

(86) PCT No.: PCT/US2015/030708
§ 371 (c)(1),
(2) Date: Nov. 14, 2016

(87) PCT Pub. No.: WO2015/175748
PCT Pub. Date: Nov. 19, 2015

(65) Prior Publication Data
US 2017/0088586 A1 Mar. 30, 2017

Related U.S. Application Data

(60) Provisional application No. 61/993,112, filed on May 14, 2014, provisional application No. 61/993,135, filed on May 14, 2014.

(51) Int. Cl.
| | | |
|---|---|---|
| C07K 14/00 | (2006.01) |
| C07K 14/47 | (2006.01) |
| G01N 33/53 | (2006.01) |
| A61K 38/16 | (2006.01) |
| C12N 15/10 | (2006.01) |
| C12Q 1/6834 | (2018.01) |
| G01N 30/02 | (2006.01) |
| A61K 38/00 | (2006.01) |

(52) U.S. Cl.
CPC ............ C07K 14/001 (2013.01); A61K 38/16 (2013.01); C07K 14/4703 (2013.01); C12N 15/1062 (2013.01); C12Q 1/6834 (2013.01); G01N 30/02 (2013.01); G01N 33/5308 (2013.01); A61K 38/00 (2013.01); G01N 2030/027 (2013.01)

(58) Field of Classification Search
CPC .................................................. C07K 14/001
See application file for complete search history.

(56) References Cited

U.S. PATENT DOCUMENTS

| | | | |
|---|---|---|---|
| 2006/0110388 A1* | 5/2006 | Davies | C07K 16/18 424/145.1 |
| 2010/0010072 A1 | 1/2010 | Dmitrovsky et al. | |
| 2010/0273673 A1* | 10/2010 | Kim | G01N 33/5008 506/9 |
| 2010/0285471 A1 | 11/2010 | Croce et al. | |
| 2011/0076676 A1* | 3/2011 | Darnell | C12N 15/1003 435/6.1 |
| 2011/0230367 A1 | 9/2011 | Yu et al. | |
| 2012/0087992 A1* | 4/2012 | Ju | A61K 31/7088 424/649 |
| 2012/0094374 A1* | 4/2012 | Bentwich | C12N 15/111 435/320.1 |
| 2012/0122216 A1* | 5/2012 | Esau | C12N 15/111 435/375 |
| 2012/0214208 A1* | 8/2012 | Patrick | C12N 9/93 435/91.52 |
| 2013/0245106 A1* | 9/2013 | de Fougerolles | A61K 48/00 514/44 R |
| 2013/0259923 A1* | 10/2013 | Bancel | A61K 48/005 424/450 |

OTHER PUBLICATIONS

Brioschi et al., 2010, Down-regulation of MicroRNAs 222/221 in Acute Myelogenous Leukemia with Deranged Core-Binding Factor Subunits, Neoplasia, 12(11): 866-876.*
Brognara, Eleonora et al.; "Peptide nucleic acids targeting miR-221 modulate p27KIP1 expression in breast cancer MDS-MB-231 cells"; International Journal of ncology; 2012; 41; pp. 2119-2127.
Millward, Steven W. et al.; "Design of Cyclic Peptides That Bind Protein Surfaces with Antibody-Like Affinity"; ACS Chem Biol; Sep. 21, 2007; 2(9); pp. 625-634.
Ren, Guodong et al.; "Regulation of miRNA abundance by RNA binding protein TOUGH in *Arabidopsis*"; PNAS; Jul. 31, 2012; 109(31); pp. 12817-12821.

* cited by examiner

*Primary Examiner* — Amber D Steele
(74) *Attorney, Agent, or Firm* — DLA Piper LLP (US)

(57) ABSTRACT

Disclosed are peptides which specifically bind to preselected pre-miRNA or pri-miRNA targets, methods of down-regulating EMT in a cell using such peptides, and methods of preparing such peptides. Also provided are therapeutic compositions comprising peptides that specifically bind a preselected cancer marker which is a peptide or which is a pre-miRNA or a pri-miRNA and methods of treatment using the same.

8 Claims, 10 Drawing Sheets
Specification includes a Sequence Listing.

Labeled peptide assay in PBS-Tween buffer at RT 0.36nM in PBST at RT by FP

SEQUENCE LISTING

```
<160> NUMBER OF SEQ ID NOS: 17

<210> SEQ ID NO 1
<211> LENGTH: 90
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
```

```
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t

<400> SEQUENCE: 1
taatacgact cactataggg acaattacta tttacaatta caatgnnsnn snnsnnsnns    60
nnsnnsnnsn nsaagtctac agcgggtgcg                                    90

<210> SEQ ID NO 2
<211> LENGTH: 41
<212> TYPE: DNA
<213> ORGANISM: Artificial Sequence
<220> FEATURE:
<223> OTHER INFORMATION: Synthetic DNA

<400> SEQUENCE: 2
aatacgactc actataggga caattactat ttacaattac a                       41

<210> SEQ ID NO 3
<211> LENGTH: 15
<212> TYPE: DNA
<213> ORGANISM: Artificial Sequence
<220> FEATURE:
<223> OTHER INFORMATION: Synthetic Primer

<400> SEQUENCE: 3
cgcacccgct gtaga                                                    15

<210> SEQ ID NO 4
<211> LENGTH: 27
<212> TYPE: DNA
<213> ORGANISM: Artificial Sequence
<220> FEATURE:
<223> OTHER INFORMATION: oligonucleotide splint

<400> SEQUENCE: 4
tttttttttt ttcgcacccg ctgtaga                                       27

<210> SEQ ID NO 5
<211> LENGTH: 21
<212> TYPE: DNA
<213> ORGANISM: Artificial Sequence
<220> FEATURE:
<223> OTHER INFORMATION: Reverse Primer

<400> SEQUENCE: 5
gcctgatgtg cttgcggtcc c                                             21

<210> SEQ ID NO 6
<211> LENGTH: 24
<212> TYPE: DNA
<213> ORGANISM: Artificial Sequence
<220> FEATURE:
<223> OTHER INFORMATION: oligonucleotide splint

<400> SEQUENCE: 6
tttttttttt ttgcctgatg tgct                                          24

<210> SEQ ID NO 7
<211> LENGTH: 40
```

```
<212> TYPE: RNA
<213> ORGANISM: Artificial Sequence
<220> FEATURE:
<223> OTHER INFORMATION: Pre-miRNA-221

<400> SEQUENCE: 7
acaauguaga uuucuguguu cguuaggcaa cagcuacauu                              40

<210> SEQ ID NO 8
<211> LENGTH: 40
<212> TYPE: RNA
<213> ORGANISM: Artificial Sequence
<220> FEATURE:
<223> OTHER INFORMATION: Pre-miRNA-221 with point mutation 1

<400> SEQUENCE: 8
acaauuuaga uuucuguguu cguuaggcaa cagcuacauu                              40

<210> SEQ ID NO 9
<211> LENGTH: 40
<212> TYPE: RNA
<213> ORGANISM: Artificial Sequence
<220> FEATURE:
<223> OTHER INFORMATION: Pre-miRNA-221 with point mutation 2

<400> SEQUENCE: 9
acaauguagc uuucuguguu cguuaggcaa cagcuacauu                              40

<210> SEQ ID NO 10
<211> LENGTH: 40
<212> TYPE: RNA
<213> ORGANISM: Artificial Sequence
<220> FEATURE:
<223> OTHER INFORMATION: Pre-miRNA-221 with point mutation 3

<400> SEQUENCE: 10
acaauguaga uuucuuuguu cguuaggcaa cagcuacauu                              40

<210> SEQ ID NO 11
<211> LENGTH: 40
<212> TYPE: RNA
<213> ORGANISM: Artificial Sequence
<220> FEATURE:
<223> OTHER INFORMATION: Pre-miRNA-221 with point mutation 4

<400> SEQUENCE: 11
acaauguaga uuucuguguc cguuaggcaa cagcuacauu                              40

<210> SEQ ID NO 12
<211> LENGTH: 40
<212> TYPE: RNA
<213> ORGANISM: Artificial Sequence
<220> FEATURE:
<223> OTHER INFORMATION: Pre-miRNA-221 with point mutation 5

<400> SEQUENCE: 12
acaauguaga uuucuguguu cguuaggcaa caucuacauu                              40

<210> SEQ ID NO 13
<211> LENGTH: 40
<212> TYPE: DNA
<213> ORGANISM: Artificial Sequence
<220> FEATURE:
<223> OTHER INFORMATION: ssDNA

<400> SEQUENCE: 13
```

```
acaatgtaga tttctgtgtt cgttaggcaa cagctacatt                             40

<210> SEQ ID NO 14
<211> LENGTH: 40
<212> TYPE: DNA
<213> ORGANISM: Artificial Sequence
<220> FEATURE:
<223> OTHER INFORMATION: dsDNA

<400> SEQUENCE: 14
acaatgtaga tttctgtgtt cgttaggcaa cagctacatt                             40

<210> SEQ ID NO 15
<211> LENGTH: 37
<212> TYPE: RNA
<213> ORGANISM: Artificial Sequence
<220> FEATURE:
<223> OTHER INFORMATION: pre-miRNA-21

<400> SEQUENCE: 15
gacugauguu gacuguugaa ucucauggca acaccag                                37

<210> SEQ ID NO 16
<211> LENGTH: 32
<212> TYPE: RNA
<213> ORGANISM: Artificial Sequence
<220> FEATURE:
<223> OTHER INFORMATION: pre-miRNA-122

<400> SEQUENCE: 16
augguguuug ugucuaaacu aucaaacgcc au                                     32

<210> SEQ ID NO 17
<211> LENGTH: 38
<212> TYPE: RNA
<213> ORGANISM: Artificial Sequence
<220> FEATURE:
<223> OTHER INFORMATION: pre-miRNA-222

<400> SEQUENCE: 17
aguguagauc cugucuuucg uaaucagcag cuacaucu                               38
```

METHODS AND COMPOSITIONS FOR CONTROLLING GENE EXPRESSION AND TREATING CANCER

CROSS-REFERENCE TO RELATED APPLICATIONS

This application is a U.S. National State application based on PCT International Application No. PCT/US2015/030708, filed on May 14, 2015, entitled "Methods and Compositions for Controlling Gene Expression and Treating Cancer," and claims the benefit of U.S. Provisional Application No. 61/993,135, filed on May 14, 2014, entitled "Methods and Compositions for Treating Cancer," and U.S. Provisional Application No. 61/993,112, filed on May 14, 2014, entitled "Methods and Compositions for Controlling Targeted Gene Expression," all of which are hereby expressly incorporated by reference into the present application.

FIELD OF THE INVENTION

This disclosure relates to the fields of molecular biology and cancer therapy. More specifically, the disclosure relates to therapeutic micro mRNA-specific peptides.

BACKGROUND OF THE INVENTION

Metastasis is the primary cause of death in cancer patients. Particularly aggressive forms of cancer, such as pancreatic ductal adenocarcinoma or basal-like breast cancer, are highly lethal in part due to their tendency to metastasize, often prior to diagnosis. Metastatic tumors are often characterized by intrinsic resistance to traditional chemo- and radiotherapies, making them an important target for the development of novel therapies.

Not all cancer cells within a primary tumor drive metastasis. Instead, only a small subsection of the tumor cell population, called cancer stem cells (CSCs), are capable of initiating metastasis and the formation of novel tumors. CSC subtypes have been identified in breast, pancreatic, prostate, colon, brain and liver cancers, as well as leukemias and are inherently resistant to chemo- and radiotherapy which target proliferating cells. Unfortunately, monotherapy with cytotoxic agents actually have been found to enhance the relative proportion of CSC cells within a tumor. The CSCs are then capable of reestablishing tumors post-therapy, leading to the generation of novel masses characterized by cancer cell populations with increased drug resistance and enhanced metastatic ability.

The acquisition of CSC properties is closely associated with the activation of the "epithelial-to-mesenchymal transition" ("EMT") and concomitant expression surface markers notable in highly aggressive and invasive cancers. The ability of a tumor cell to acquire CSC characteristics and form metastasis seems to be due in part to the EMT. However, EMT is also a requirement for normal development and repair mechanisms such as embryogenesis, and fibrosis and wound healing, and in all cases entails morphological and phenotypic changes to cells.

A number of proteins and transcription factors have been found to induce EMT, such as, but not limited to, various transcription factors and hormones. The altered expression of these factors can thus affect the status of EMT, and hence, embryonic development, fibrosis and wound healing, and the development of cancer.

EMT is regulated in part at a post-transcriptional level via miRNAs. miRNAs are small, non-coding RNAs that regulate translation on a post-transcriptional level by causing mRNA degradation or repressing mRNA translation. miRNAs and mature miRNAs can function as oncogenes and are differentially expressed in cancer versus healthy cells.

One particular miRNA, miRNA-221, is significantly upregulated in a large number of cancers, and its expression characterizes the most aggressive forms of human solid tumors. The overexpression of miRNA-221, sometimes by up to 70-fold compared to healthy tissue, has been documented in hepatocarcinoma, non-small cell lung cancer, pancreatic, melanoma, breast, thyroid and multiple myeloma, among others (*Cancer Cell* 16:498-509 (2009)). As used herein, the terms "overexpression" or "elevated expression" means more than 2-fold. miRNA 221 as well as miRNA 222 also function as regulators of the EMT in basal-like breast cancers and have multiple targets, at least two of which function to modulate the EMT pathway.

Gene expression includes transcription of the DNA to RNA, and the translation of RNA into proteins and peptides. Controlling the expression of certain genes in a cell is a useful tool for increasing or inhibiting the growth of cells, and for increasing and inhibiting the synthesis of certain desired native or genetically engineered cellular products such as those involved in the production of beneficial enzyme and hormone synthesis or which are cancer markers.

One method of treating cancer uses antisense methodology. Antisense technology is another example of a known method of controlling the expression of cellular DNA whereby a synthesized oligonucleotide synthesized to have a particular sequence complementary to a portion of that of a targeted DNA is used to bind that DNA, thereby stopping the target DNA it from being duplicated or from being transcribed into RNA. However, this technology has not been very efficacious as many antisense oligonucleotides have difficulty crossing cell members and so are never able to contact and bind to their target oligonucleotide. In addition, antisense molecules are not targeted to one particular molecule as they can bind to both DNA and RNA having complementary nucleotide sequences and thus may have affinity for more than one target sharing that particular sequence.

Thus, what are needed are improved compositions and therapeutic methods for more specific regulation of RNA expression.

In addition, therapeutic methods and pharmaceutical compositions that can inhibit the growth of cancer and in particular, can inhibit the development of metastasis-inducing cancer stem cells are needed.

SUMMARY

It has been discovered that certain peptides ("SUPR" peptides) are able to specifically bind a preselected peptide, or a preselected premature microRNA (pre-miRNA) and/or primary transcript of microRNA (pri-miRNA) with at least nmolar affinity, and that these peptides have the ability to control gene expression, and thus have therapeutic value in mammalian subjects.

These discoveries have been exploited to develop the invention, which, in one aspect, is a therapeutic composition comprising a therapeutically effective amount of a peptide that is at least partially resistant to proteolytic digestion, is mammalian cell membrane-permeable, and that specifically binds a preselected cell marker with at least nmolar affinity, the marker being a peptide, a polypeptide, a protein, a primary transcript of a microRNA (pri-miRNA), and/or a premature microRNA (pre-miRNA). In some embodiments, the cell marker to which the peptide of the therapeutic composition specifically binds is a cancer cell marker or a cancer stem cell marker. In some embodiments the cancer cell marker is pre-miRNA-221. In certain embodiments, the protein specifically binds pre-miRNA-221 and/or pri-miRNA-221. In one embodiment, the therapeutic composition comprises an additional, different cancer therapeutic drug.

In another aspect, the present disclosure provides a method of treating cancer in a mammalian patient, the cancer comprising a cell having elevated miRNA-221 expression. The method comprises administering a therapeutically effective amount of a therapeutic composition to the subject to inhibit or decrease expression of miRNA-221 in the cancer cell, the therapeutic composition comprising a therapeutically effective amount of a peptide that is at least partially resistant to proteolytic digestion, is mammalian cell membrane-permeable, and that specifically binds a primary transcript of microRNA-221 (pri-miRNA-221) and/or pre-mature microRNA-221 (pre-miRNA-221) with at least nmolar affinity. In some embodiments, the cancer is hepatocarcinoma, non-small cell lung cancer, pancreatic cancer, melanoma, breast cancer, thyroid cancer, or multiple myeloma. In one embodiment, the patient is further treated with an additional cancer therapeutic. In another embodiment, the therapeutic composition further comprises an additional cancer therapeutic.

In a different aspect, the disclosure provides a method of inhibiting the growth or development of a cancer cell, comprising down-regulating the expression of mRNA-221 in that cell by contacting the cell with a peptide specific for pre-miRNA-221 and/or pri-miRNA-221, the peptide binding pre-miRNA-221 and/or pri-miRNA-221 with at least nmolar affinity, is mammalian cell membrane-permeable, and is at least partially proteolysis-resistant. In one embodiment, the cancer cell is a cancer stem cell. In one embodiment, EMT is inhibited in the cancer stem cell contacted with the peptide. In certain embodiments, I the cancer cell is a hepatocarcinoma, non-small cell lung cancer, pancreatic cancer, melanoma, breast cancer, thyroid cancer, or multiple myeloma cell. In some embodiments, the method results in a decreased expression of a surface marker on the cell.

Also provided is a method of down-regulating epithelial-to-mesenchymal transition (EMT) in a cancer stem cell, by contacting the cell with a peptide that binds pre-miRNA-221 and/or pri-miRNA-221 with at least nmolar affinity, is mammalian cell membrane-permeable, and is at least partially proteolysis-resistant. In some embodiments, the method results in a decreased expression of a surface marker on the cell.

In yet another aspect, a peptide is provided which specifically binds a preselected peptide, polypeptide, protein, pre-miRNA, and/or pri-miRNA with at least nmolar affinity, and which is at least partially proteolysis-resistant. In some embodiments, the peptide is mammalian cell membrane-permeable. In certain embodiments, the peptide specifically binds pre-miRNA-221 or pri-miRNA-221. In some embodiments, the peptide has a binding affinity of about 19 pM to about 999 nM. In certain embodiments, the peptide specifically binds a cancer stem cell marker. In one embodiment, the peptide binds pre-miRNA-221 or pri-miRNA-221, thereby downregulating the expression of miRNA-221 in a cancer cell or cancer stem cell.

In another aspect, the disclosure provides a method of down-regulating epithelial-to-mesenchymal transition (EMT) in a cell, comprising contacting the cell with a peptide which specifically binds pre-miRNA-221 and/or pri-mRNA-221 with at least nmolar affinity and which is at least partially proteolysis-resistant. In one embodiment, the binding of the peptide to pre-miRNA221 and/or pri-miRNA-221 downregulates the synthesis of an EMT inducer. In some embodiments, the cell is a cancer cell or a cancer stem cell. In one embodiment, expression of a surface marker on the cell is decreased when the cell is contacted with the peptide. In certain embodiments, the peptide is mammalian cell membrane-permeable.

In yet another aspect, the disclosure provides a method of preparing and screening for a peptide which binds a preselected pre-miRNA, pri-miRNA, protein, polypeptide, and/or protein with at least nmolar affinity, and which is at least partially protease-resistant. The method comprises preparing an mRNA library by transcribing a plurality of RNAs from a plurality of synthetic DNAs with random base incorporation; preparing a plurality of peptides by translation from the mRNA library in a translational system; linking the resulting peptides to the mRNAs encoding the peptides to form a plurality of peptide fusion products; contacting the peptide fusion products with a preselected protein target, polypeptide target, peptide target, pre-miRNA target, and/or pri-miRNA target, the fusion products which are specific for the protein target, polypeptide target, peptide target, premiRNA target, and/or pri-miRNA target, binding to the target; and isolating the peptide fusion products bound to the pre-miRNA target, the pri-miRNA target, the protein target, the polypeptide target, and/or the peptide target.

In certain embodiments, the contacting step is performed in the presence of a competitor RNA, and in a particular embodiment, the competitor RNA is tRNA or a tRNA mimetic. In some embodiments. the preselected miRNA and/or pre-miRNA is pre-miRNA-221 or pri-miRNA-221.

In some embodiments, the isolating step comprises immunoprecipitating the peptide fusion products bound to the pre-miRNA target, the pri-miRNA target, the protein target, the polypeptide target, and/or the peptide target. In certain embodiments, the method further comprises selecting for fusion products which are membrane-permeable, and in one embodiment, the fusion products are selected by Regis IAM HPLC. In some embodiments, the method further comprises subjecting the fusion products to proteolysis, and selecting those which are at least partially resistant to degradation. In a particular embodiment, the fusion products are subjected to proteolysis with P450 enzymes.

BRIEF DESCRIPTION OF FIGURES

The foregoing and other objects of the present disclosure, the various features thereof, as well as the invention itself may be more fully understood from the following description, when read together with the accompanying drawings in which.

DESCRIPTION

The issued U.S. patents, allowed applications, published foreign applications, and references that are cited herein are hereby incorporated by reference in their entirety to the same extent as if each was specifically and individually indicated to be incorporated by reference. Patent and scientific literature referred to herein establishes knowledge that is available to those of skill in the art.

Unless otherwise defined, all technical and scientific terms used herein have the same meaning as commonly understood by one of ordinary skill in the art to which this invention belongs.

I. SUPR Peptides

The present disclosure is directed to the preparation and use of Scanning Unnatural Protease Resistant (SUPR) peptides for the control of gene expression by specifically targeting certain pre-miRNA or pri-miRNA targets or certain peptide targets in preselected cells. A SUPR peptide has the ability to bind a specific peptide or certain pre-miRNA or pri-miRNA structures with antibody-like affinities (nM or better) and specificities. They are resistant to proteolysis and evade modification, e.g., by P450 enzymes in microsomes. These peptides are also resistant to modification by human serum.

Figure 2:
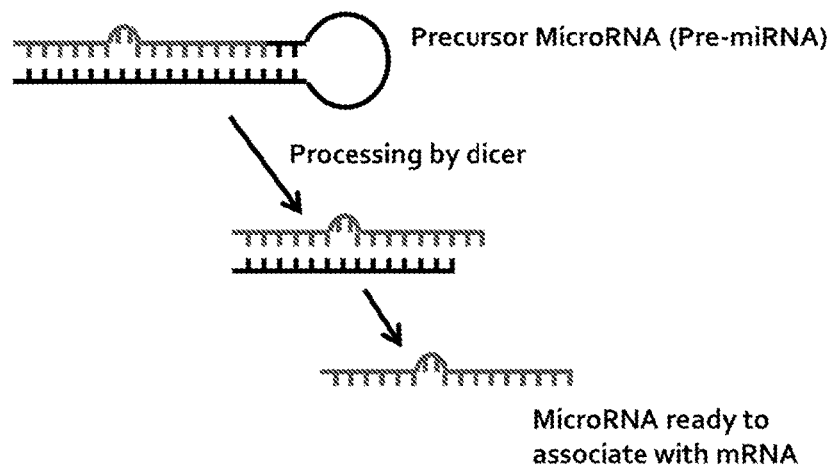
FIG. 2 is a diagrammatic representation of the preparation of miRNA from precursor miRNA (pre-miRNA) and shows the difference in structure of these RNAs.

The peptides of the present disclosure can be designed to be very specific for RNAs with a certain structure. The peptides recognize a tRNA-like structure having a bulge and hairpin (FIG. 2), whereas they have difficulty targeting linear RNA (such as mRNA). Pre-miRNA and pri-miRNA, which are both specifically recognized by SUPR peptides, have this bulge and hairpin structure. These RNA structures are later processed to become mature miRNA, which do not have this structure, and which is not recognized by SUPR peptide.

Figure 4:
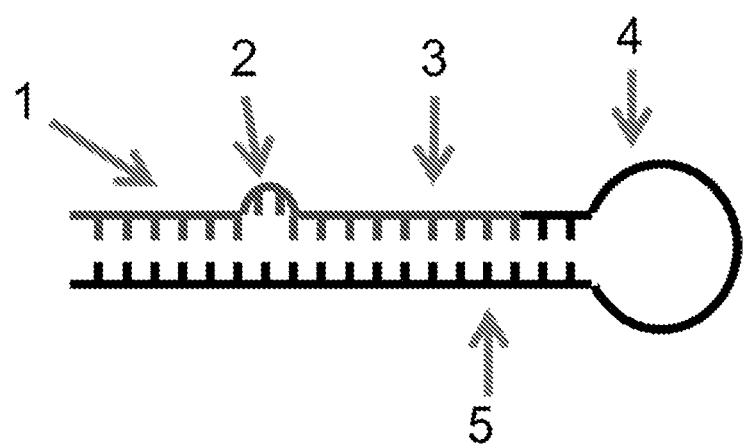
FIG. 4 is a diagrammatic representation of the single point mutations made to the pre-miRNA before testing for binding affinity, and shows the approximate locations of the point mutations analyzed.
Figure 5A:
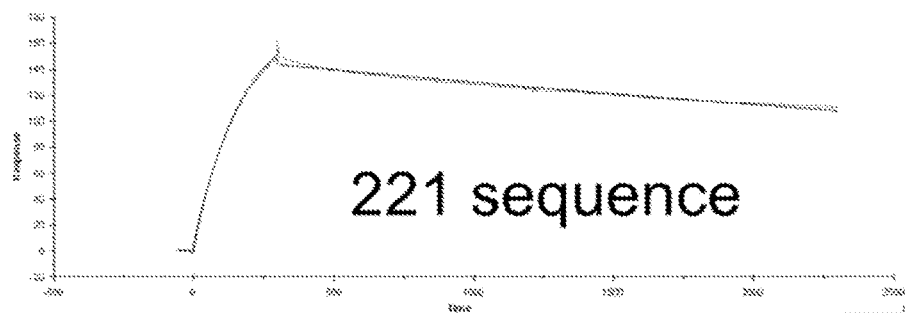
FIG. 5A is a graphic representation of the binding affinity of the peptide for pre-miRNA 221 no point mutations.
Figure 5B:
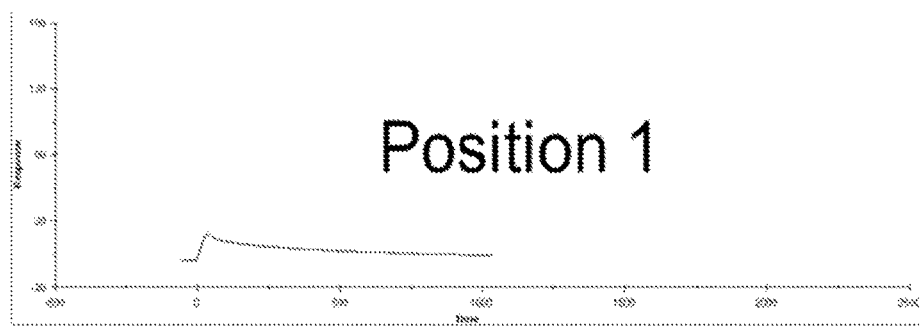
FIG. 5B is a graphic representation of the binding affinity of the peptide for pre-miRNA 221 having a point mutation at position 1.
Figure 5C:
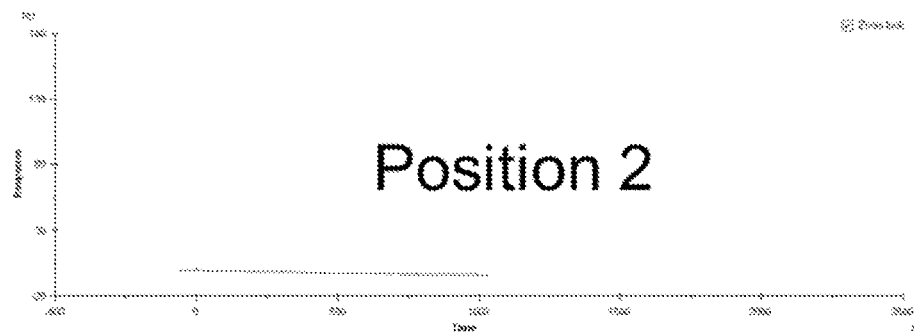
FIG. 5C is a graphic representation of the binding affinity of the peptide for pre-miRNA 221 having a point mutation at position 2.
Figure 5D:
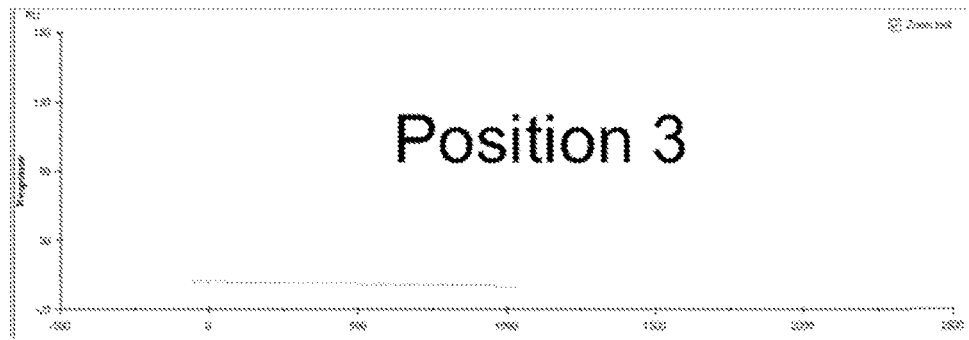
FIG. 5D is a graphic representation of the binding affinity of the peptide for pre-miRNA 221 having a point mutation at position 3.
Figure 5E:
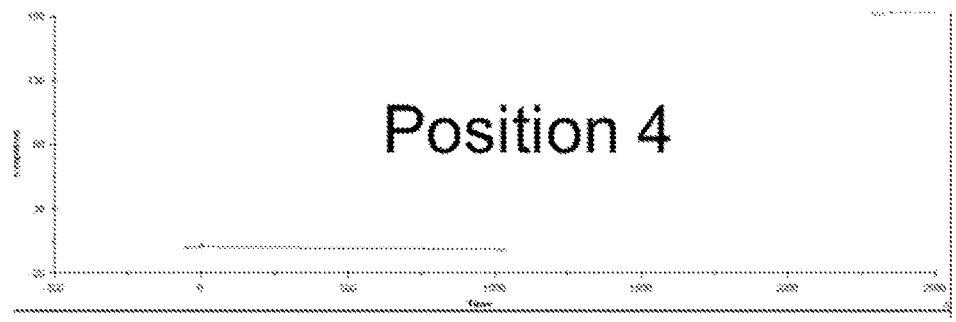
FIG. 5E is a graphic representation of the binding affinity of the peptide for pre-miRNA 221 having a point mutation at position 4.
Figure 5F:
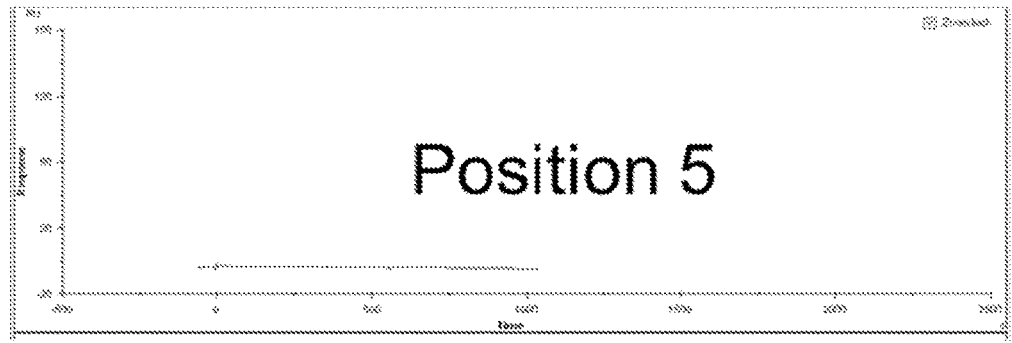
FIG. 5F is a graphic representation of the binding affinity of the peptide for pre-miRNA 221 having a point mutation at position 5.
Figure 6A:
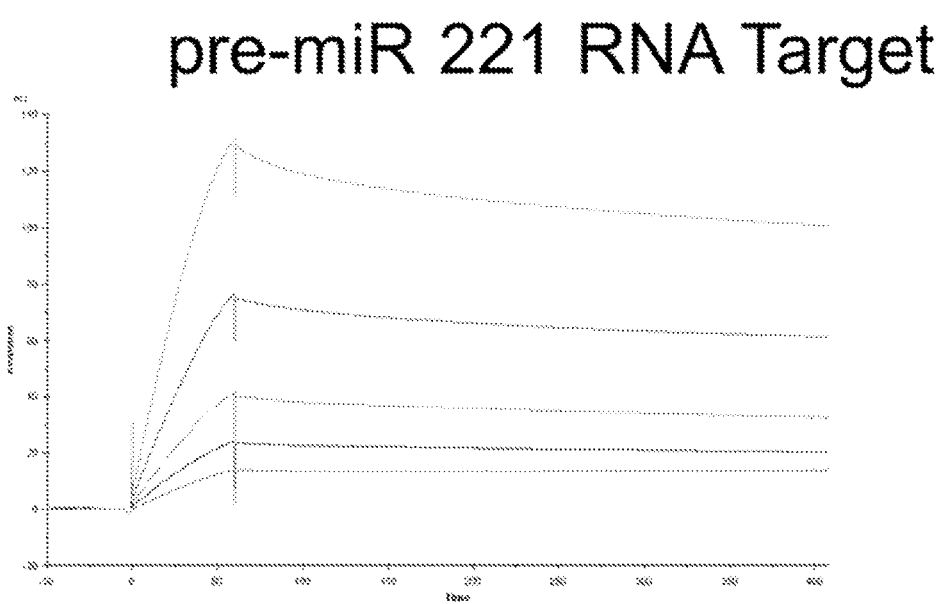
FIG. 6A is a graphic representation of the binding specificity of a peptide according to the disclosure for pre-miRNA-221 at different concentrations.
Figure 6B:
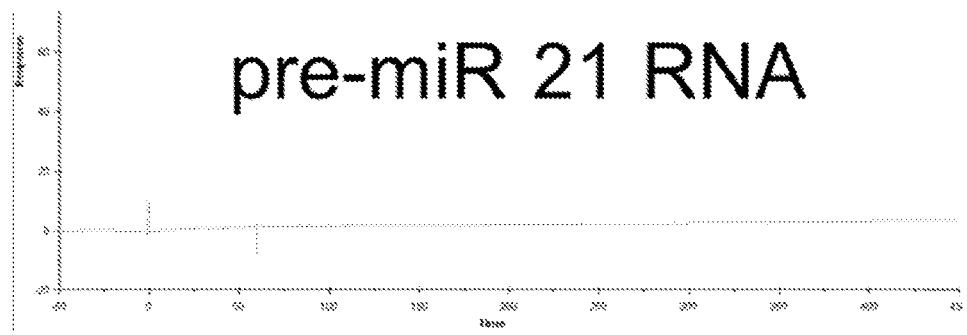
FIG. 6B is a graphic representation of the binding specificity of a peptide according to the disclosure for pre-miRNA-21.
Figure 6C:
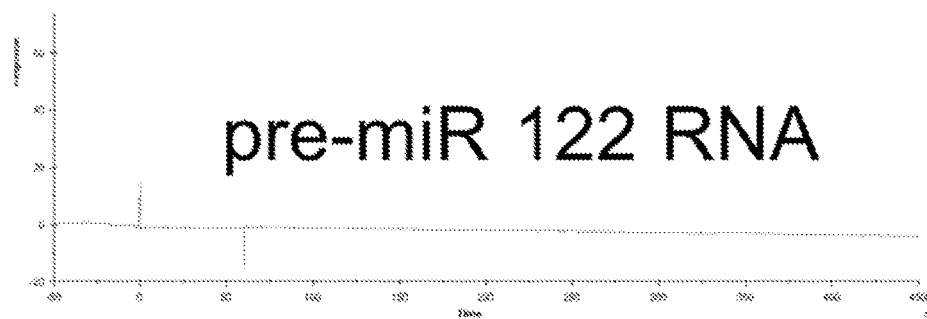
FIG. 6C is a graphic representation of the binding specificity of a peptide according to the disclosure for pre-miRNA-122.
Figure 6D:
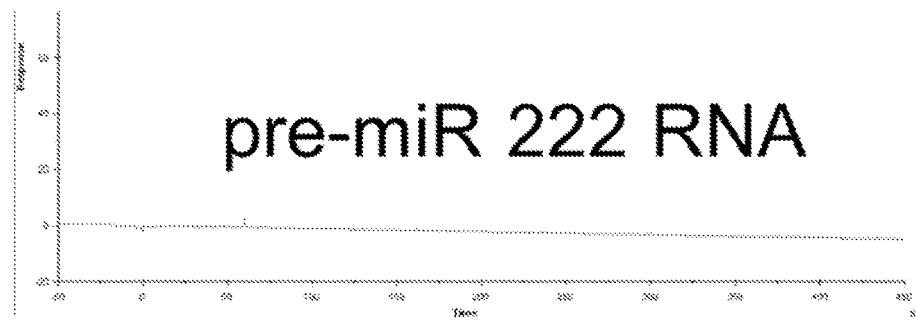
FIG. 6D is a graphic representation of the binding specificity of a peptide according to the disclosure for pre-miR-222.

Additionally, these peptides can distinguish between different pri-miRNAs and different pre-miRNAs with slightly different structures. Their specificity was demonstrated using pre-miRNA targets with various single point mutations made in different locations along its structure (FIG. 4). The binding affinity of the peptide to these targets with point mutations was then tested. 4 of 5 point mutations resulted in no binding to the target (FIGS. 5A-5E), whereas having the fifth point mutation resulted in an 80-fold drop in affinity (FIG. 5F). Thus, only the correct miRNA is targeted; there is no association with the genome. They can also distinguish different miRNA sequences (FIGS. 6A-6D and EXAMPLE 4).

Figure 7A:
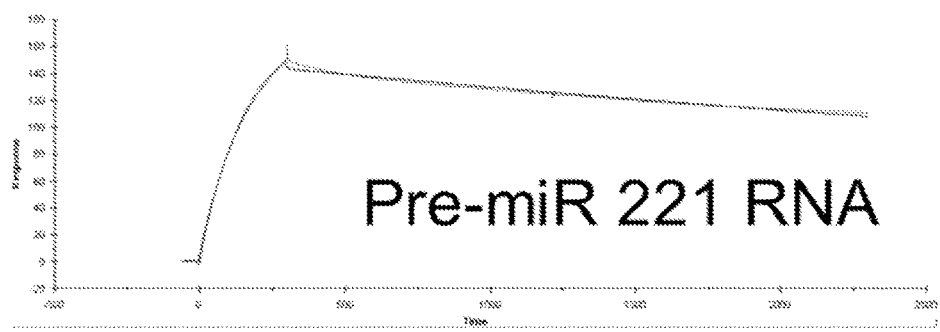
FIG. 7A is a graphic representation of the binding affinity of the peptide for pre-miRNA-221 having no point mutations.
Figure 7B:
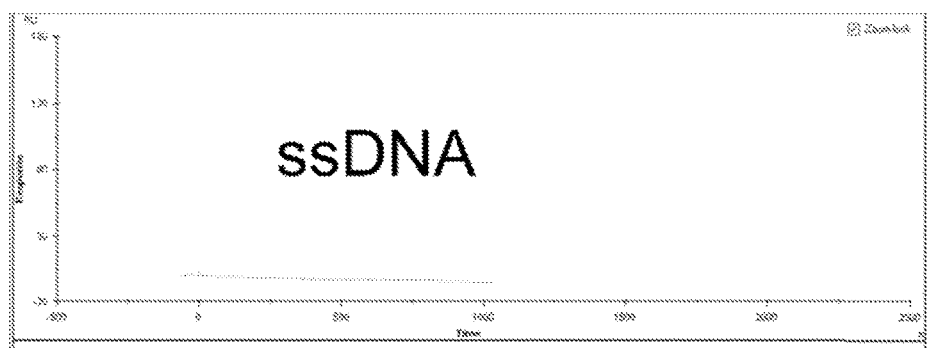
FIG. 7B is a graphic representation of a scan showing that the peptide has no affinity for single-stranded DNA (ss DNA) with the equivalent sequence as pre-miRNA-221.
Figure 7C:
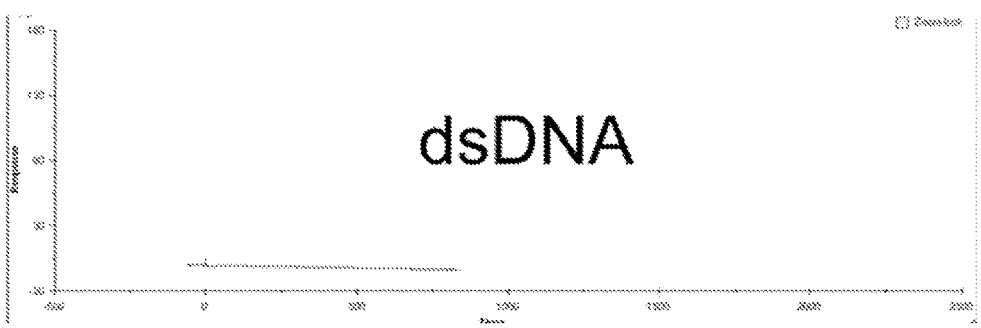
FIG. 7C is a graphic representation of a scan showing that the peptide has no affinity for double-stranded DNA (ds DNA) with the equivalent sequence as pre-miRNA-221 and its complement.
Figure 8A:
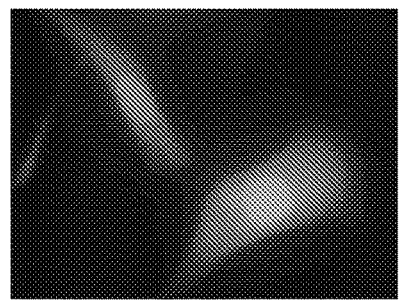
FIGS. 8A to 8D are photographic representations of fluorescence micrographs of DAP 1-stained live HS766T pancreatic cancer cells to which the peptide was administered at 10 μm showing that the peptides according to the disclosure are entering cells.
Figure 8B:
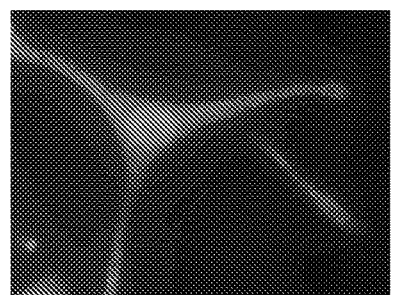
Figure 8C:
Figure 8D:
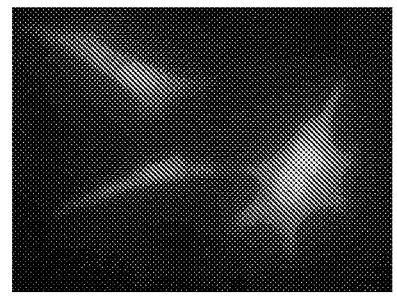
Figure 9:
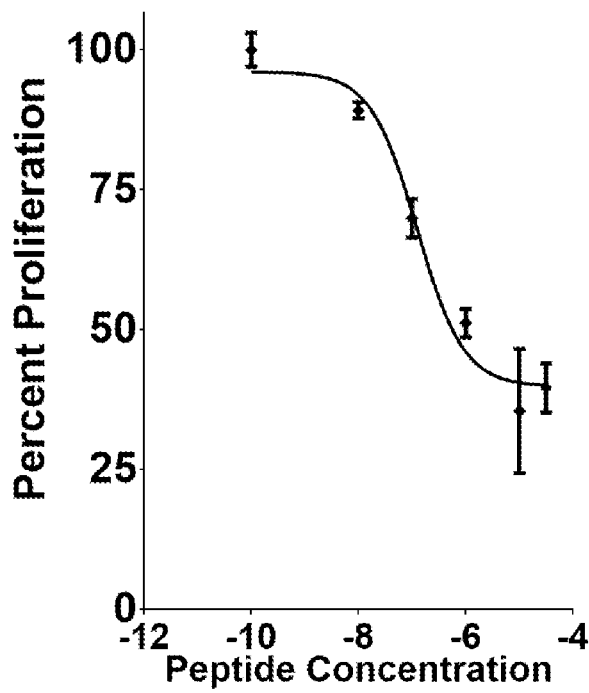
FIG. 9 is a graphic representation showing percent proliferation of HS766T pancreatic cancer cells after treatment with different concentrations of peptide.

Also, the ability of these peptides to distinguish DNA from RNA and, unlike antisense molecules, to target only RNA was demonstrated. DNA and RNA of the same sequence tend to form different structures. FIG. 7A shows the specificity of the peptide for the RNA structure. No binding was observed to single- (ss) or double-stranded (ds) DNA with the equivalent sequence as the miRNA target (FIGS. 7B-7C, and EXAMPLE 4).

Additionally, these peptides are readily cell-permeable, and have shown to penetrate a variety of mammalian cell types, including, but not limited to, HeLa, COS, HS766T pancreatic cancer, neurons, 293T, and 3T3 mouse cells.

SUPR peptides according to the disclosure can be prepared by being generated from RNA transcribed from synergistic DNA (SEQ ID NO:1) with randomized base incorporation in vitro in a eukaryotic cell lysate, such as a rabbit reticulocyte lysate, through the addition of unnatural amino acids. They can also be generated using any peptide library generation technology including, but not limited to, phage display, mRNA display, and ribosome display. After synthesis, peptides are subjected to post-translational cyclization to mRNA display libraries, enabling the creation of millions to trillions of peptidomimetics. A library was created with approximately 500 billion peptides.

Figure 1:
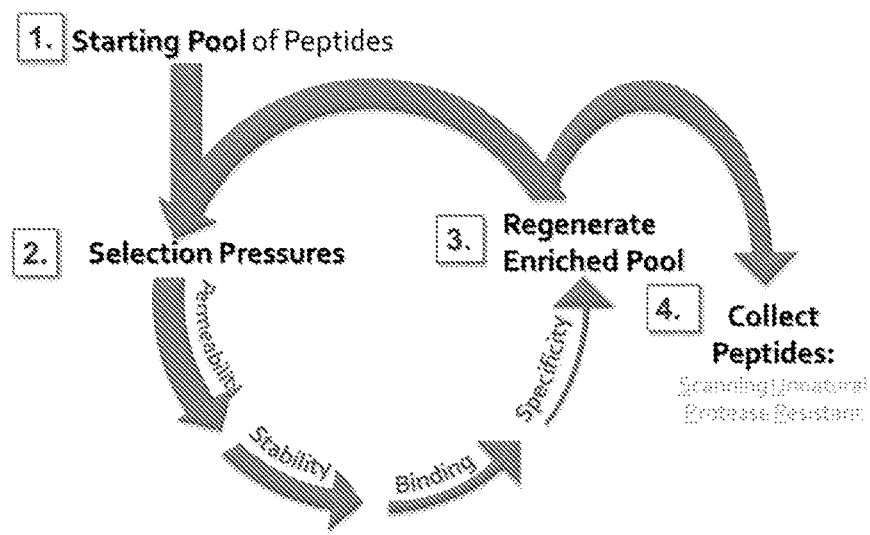
FIG. 1 is a diagrammatic representation delineating the present strategy for screening and selecting peptides.

Peptides are then screened as shown in FIG. 1. The peptide library is subjected to separation by HPLC, e.g., using a Regis IAM permeability HPLC column designed to mimic a phospholipid bilayer. In this system molecules with larger retention times tend to be more membrane permeable. The fraction of the library with the longest retention time is used for further selection.

This fraction of the library is then proteolyzed. The remaining fraction can be immunoprecipitated with immobilized target pre-miRNA in the presence of a molar excess of competitor RNA (such as tRNA) to remove peptides with nonspecific RNA binding. Alternatively, the library is immunoprecipitated in the presence of competitor RNA without proteolysis and column chromatography.

II. Control of Cancer Cell Growth/Development

Because of their unique characteristics, the peptides according to the disclosure are useful for controlling cancer cell growth and/or development. For example, a peptide according to the disclosure specifically targeted to a pre-miRNA known to be a cancer cell marker can be useful to inhibit the growth of cancer cells having that particular marker. Pre-miRNA-221 is one such target found on cancer stem cells to which a particular peptide according to the disclosure can specifically bind. Pre-miRNA-221 is overexpressed in a number of different cancer cells (Table 1), and leads to the inhibition of the expression of certain proteins in those cells (see, e.g., EXAMPLE 3F).

TABLE 1

221 pre-microRNA overexpression in the following cancers:

| Glioblastoma | Pancreatic | Prostate |
|---|---|---|
| Ovarian | Bladder | Liver (HCC) |
| Lung (NSCLC) | Papillary Thyroid | |

Overexpression leads to knock-down of:

| p27-Kip1 | PTEN | TIMP3 | p57 |
|---|---|---|---|
| PUMA | TRPS1 | ERα-FOXO3 | DDIT4 |
| Bim | p27-Kip2 | Bmf | e-cadherin |
| A DIPORI | CD44 | β-actin | |

Peptides according to the disclosure that specifically target pre-miRNA-221 are useful as therapeutic targeting agents for pre-miRNA-221$^+$ cancer stem cells, as their antibody-like affinities and specificities lead to enhanced accumulation in tumors, and their inhibition of miRNA function in cancer stem cells leads to blocking tumor metastases. This was demonstrated in HS766T liver cancer cells contacted with a peptide according to the invention and subjected to ion torrent sequencing to detect the changes in expression of various proteins when the peptide is administered (FIGS. 8A-8D and FIG. 9). Accordingly, the disclosure provides methods of down-regulating epithelial-to-mesenchymal transition (EMT) in a cancer stem cell, by contacting the cell with a peptide that binds pre-miRNA-221 and/or pri-miRNA-221 with at least nmolar affinity, is mammalian cell membrane-permeable, and is at least partially proteolysis-resistant down-regulating epithelial-to-mesenchymal transition (EMT) in a cancer stem cell, by contacting the cell with a peptide that binds pre-miRNA-221 and/or pri-miRNA-221 with at least nmolar affinity, is mammalian cell membrane-permeable, and is at least partially proteolysis-resistant.

Figure 10:
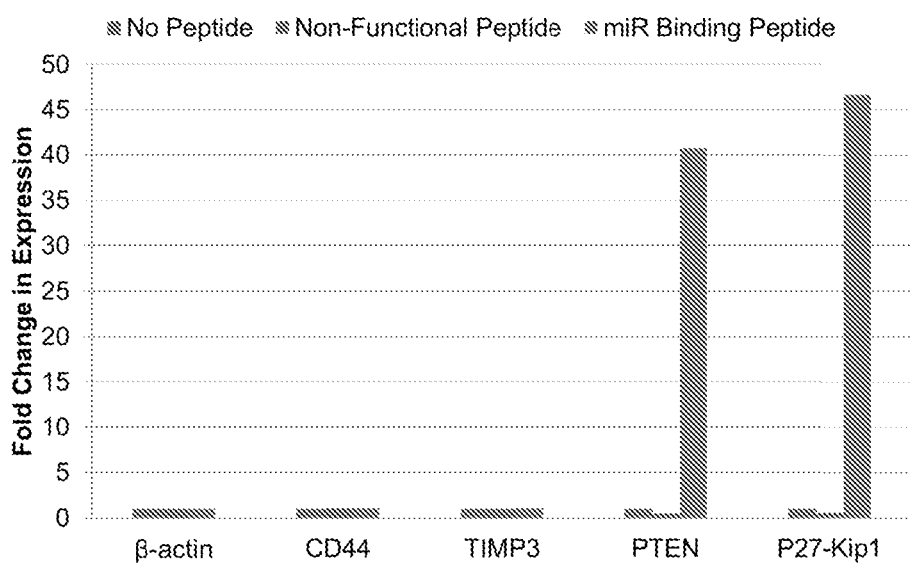
FIG. 10 is a graphic representation of x-fold change in expression of β-actin, TIMP3, Erα-FOXOS, TRPS1, PTEN, and P27-Kip1, in the presence or absence of peptides inhibiting pre-miRNA-221 processing.

FIG. 10 shows the expression level changes in various proteins in the treated cell. Typical expression level changes from antisense technology ranges from 50% to 2-fold. However, two proteins exhibited expression level changes of 40-fold. This demonstrates the ability of the peptides to control gene expression in a cancer cell which expresses the target.

III. Therapeutic Compositions and Methods of Treatment

The present disclosure also provides a therapeutic composition comprising the peptides according to the disclosure and a pharmaceutically-acceptable carrier suitable for administration to a mammalian subject (e.g., such as a human). Any suitable carrier known in the art for the administration of a peptide may be used. Carriers include, but are not limited to, a solid, liquid, or a mixture of a solid and a liquid. The carriers may take the form of capsules, tablets, pills, powders, lozenges, suspensions, emulsions, or syrups. The carriers may include substances that act as flavoring agents, lubricants, solubilizers, suspending agents, binders, stabilizers, tablet disintegrating agents, and encapsulating materials. Methods of preparing these compositions include the step of bringing into association a peptide according to the disclosure with the carrier and, optionally, one or more accessory ingredients.

The phrase "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The pharmaceutical compositions may conveniently be presented in unit dosage form and may be prepared by any methods well known in the art of pharmacy. The amount of peptide which can be combined with a carrier material to produce a single-dosage form will vary depending upon the subject being treated, the particular mode of administration, the particular condition being treated, among others. The amount of peptide that can be combined with a carrier material to produce a single-dosage form will generally be that amount which produces a therapeutic effect.

The therapeutic compositions are administered in a therapeutic amount to a patient in need of such treatment. Such an amount is effective in treating a cancer in the patient. This amount may vary, depending on the activity of the agent utilized, the nature and type of the cancer, and the health of the patient. The term "therapeutically-effective amount" is used to denote treatments at dosages effective to achieve the therapeutic result sought and that is capable of reducing the symptoms of the disorder in a subject. Furthermore, a skilled practitioner will appreciate that the therapeutically-effective amount of the peptide-containing therapeutic composition may be lowered or increased by fine-tuning and/or by administering more than one peptide according to the disclosure, or by administering a the peptide-containing therapeutic composition together with a second anticancer agent (e.g., classic chemotherapies such as taxol, fluorouracil, tarceva, herceptin, avastin, antisense oligo or LNA based technologies). Therapeutically-effective amounts may be easily determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al. (1993) *Diabetes* 42:1179). As is known to those in the art, the effective amount will depend on bioavailability, bioactivity, and biodegradability of the therapeutic compound. Administration may be hourly, daily, weekly, monthly, yearly, or a single event. For example, the effective amount of the peptide in the therapeutic composition may comprise from about 1 ug/kg body weight to about 100 mg/kg body weight.

Modes of administering the therapeutic compositions can be by any of a number of methods well known in the art.

These methods include local or systemic administration. Exemplary routes of administration include oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir. Methods of introduction may also be provided by rechargeable or biodegradable devices, e.g. depots. Furthermore, it is contemplated that administration may occur by coating a device, implant, stent, or prosthetic.

As described above, the therapeutic composition according to the disclosure can be administered as part of a combinatorial therapy with other agents. "Combination therapy" refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined (conjoint) effect of different therapeutic compounds.

Reference will now be made to specific examples illustrating the disclosure. It is to be understood that the examples are provided to illustrate exemplary embodiments and that no limitation to the scope of the disclosure is intended thereby.

EXAMPLES

Example 1

Naïve Selection

A. Synthesis of NMK-tRNA and Ligation to THG-73

N-methyl lysine-dCA was synthesized and ligated to THG-73 (IDT Technologies, Coralville, Iowa) according to published protocols (Millward et al. (Sep. 21, 2007) *ACS Chem Biol.*, 2(9):625-634.

B. Preparation of $MX_9K$ Library

Synthetic DNA with the sequence: 5'-TAATACGACTCACTATAGGGACAATTACTATTTACAATTACAAT-GNNSNNSN NSNNSNNSNNSNNSNNSNNSAAGTCTACAGCGGGTGCG-3' (N=A, T, C, G and S=G,C) (SEQ ID NO:1) was purchased from IDT Technologies. Base incorporation of the randomized region of the library was skewed such at there was a 34.3% chance of having a TAG codon at each position. The library was amplified via polymerase chain reaction (PCR) using 20 nM of template diluted into a PCR master solution containing Gen FP: (5'-AATACGACTCACTATAGGGACAATTACTATTTACAATTACA-3' (SEQ ID NO:2), a reverse primer (5'-CGCACCCGCTGTAGA-3') (SEQ ID NO:3), 200 μM dNTPs, and Phusion HF buffer (New England Biolabs, Ipswich, Mass.), utilizing Phusion polymerase enzyme (New England Biolabs). The amplified product was routinely purified using the Illustra GFX PCR DNA and Gel Band Purification Kit (GE Healthcare, Pasadena, Calif.).

C. Preparation of mRNAs

The $MX_9K$ library was transcribed via T7 RNA Polymerase (New England Biolabs) using manufacturer's protocols. The mRNA products were purified via ureaPAGE, followed by ethanol precipitation (R0) or Centrisep column (R1, R2, R3, R4) (Princeton Separations, Freehold Township, N.J.).

D. Ligation to F30P

The purified mRNAs were ligated to F30P (5'-dA$_{21}$[C$_9$]$_3$dAdCdC-P; C9=tri(ethylene glycol) phosphate (Glen Research, Sterling, Va.), P=puromycin (Glen Research)) via an oligonucleotide splint (5'-TTTTTTTTTTTTCGCACCCGCTGTAGA-3' (SEQ ID NO:4)) in a solution of DNA Ligase buffer and T4 DNA Ligase (New England Biolabs). The ligated mRNA product was routinely purified via PAGE and ethanol precipitation.

E. Translation 75 pmol of mRNA product was translated in 200 uL rabbit reticulocyte (Life Technologies, Grand Island, N.Y.) by addition of photolytically deprotected THG 73-ligated NMK-tRNA to a translation mixture containing 9 mM KOAc, 450 uM MgOAc and 3 mM amino acid solution. The mixture was incubated at 30° C. for 45 min. Fusion was formed by adding 9 mM KCl and 360 mM $MgCl_2$ and incubating for 15 min. at room temperature (RT). The translation was purified via addition of dT cellulose beads according to manufacturer's protocols (New England Biolabs).

F. Reverse Transcription and Digestion

For initial rounds, ligated translation template was reverse transcribed prior to digestion via the First Strand cDNA with M-MuLV kit (New England Biolabs) using manufacturer's protocols. The later rounds were amplified by reverse transcription-PCR via standard procedures by suspending templated beads (described below) in a reverse transcription-PCR master solution containing 200 nM of forward and reverse primers, 200 uM dNTPs and 1.2 mM $MgSO_4$ utilizing SuperScript III RT/Platinum Taq (Life Technologies). The library was then digested via addition of 17.4 nM α-chymotrypsin (Sigma-Aldrich, St. Louis, Mo.), 15.2 nM proteinase-K (Sigma-Aldrich), and 10 uL trypsin (Thermo-Scientific, Waltham, Mass.) in increasing durations (30 sec. to 1.5 min.), followed by filtration utilizing a Spin-X filter (Sigma-Aldrich). For later rounds, the purified translation product was digested same proteases (51.6 nM α-chymotrypsin, 45.2 nM proteinase K, 10 uL trypsin for increasing times (1 min. to 2 min.).

G. Bead Preparation and Selection

On-selection was carried out by addition of the template to 22 uL of NeutrAvidin agarose beads (ThermoScientific) fused with 1800 pmol of biotinylated miRNA-221 target in 1×PBS and increasing concentrations of yeast tRNA (Life Technologies) in each round of selection (25 ug/uL up to 5 mg/mL). The on-selection binding reaction proceeded for 1 hr at 4° C. for initial rounds, and later rounds were performed at RT. The beads were washed 3 times with cold 1×PBS and 3 times with 1×PCR buffer (R0 and R1) or RT Buffer (R2 and R3). Initial rounds underwent PCR amplification according to above protocol or underwent reverse transcription-PCR. The PCR amplified product was utilized as the template for the next selection round. Four rounds of selection (R0, R1, R2, R3) were completed.

H. Identification of Selected Sequences

The amplified PCR resulting from the third round of selection was sequenced using Ion Torrent Personal Genome Sequencer (Life Technologies) following manufacturer's protocols. Sequences were analyzed using in-house programs. Sequences were counted following orientation and rank ordering based on highest to lowest copy number.

I. Binding Analysis

Three sequences were selected resulting from Ion Torrent analysis and were ordered from IDT Technologies and amplified by PCR according to the methods outlined above. The PCR products were purified, transcribed, and translated according to methods outlined above to determine the binding strength of each sequence using the ForteBio Octet Red96 following manufacturer's procedures (Pall Corporation, Port Washington, N.Y.).

Example 2

Affinity Maturation Selection

A. Preparation of $MX_{15}$ Maturation Library

An expanded $MX_{15}$ library based on the winning sequence from the naïve selection with the strongest binding affinity was ordered from IDT. The library was amplified via PCR using the methodology outlined above with the exception of a different reverse primer (5'-GCCTGATGTGCTT-GCGGTCCC-3' (SEQ ID NO:5)) and a lower annealing temperature (48° C.).

B. Preparation of mRNA-Peptide Fusions $MX_{15}$ library was transcribed identically to that of the naïve selection and purified via Centrisep column (Princeton Separations). Purified mRNAs were ligated to F30P via an oligonucleotide splint (5'-TTTTTTTTTTTTGCCTGATGT-GCT-3' (SEQ ID NO:6)) using the methods outlined above. Translation was carried out as described above. Digestion was performed as before by addition of proteases in increasing concentrations to the translation template (38.1 nM to 71 nM α-chymotrypsin; 33.3 nM to 62.2 nM proteinase K, 10 uL-25 uL immobilized trypsin) for 2 min. On-selection was performed as previously outlined reacting the digestion product with miRNA-221-fused NeutrAvidin beads in 5 mgs/mL yeast tRNA for 1 hr at 4° C. The beads were washed and resuspended in off-selection buffer containing non-biotinylated miRNA-221 and 5 mgs/mL yeast tRNA as previously outlined. The off-selection reaction proceeded for increasing durations at increasing temperatures (48-168 hr; 4° C. to 25° C.). The beads were then washed in 1× PBS and amplified via reverse transcription-PCR as previously outlined.

C. Selection via Permeability Column

An additional selection pressure was utilized in the middle of the maturation selection; mRNA-peptide fusions prepared in the outlined method were run through a Regis IAM HPLC column for the purpose of separating RNA-peptide fusions based on membrane permeability (Regis Technologies, Inc., Morton Grove, Ill.).

After separation of the most permeable sequences using the IAM HPLC column, another round of selection was performed as outlined above.

D. Selection via HSA Beads

A final round of selection was performed against the HSA protein. Template preparation was carried out as previously described and selection was done against immobilized HSA for 1 hour. Following selection, a final step of RT-PCR was carried out in order for the resulting library to be sequenced using Ion Torrent as outlined above.

E. Identification of Selected Sequences

The amplified PCR resulting from the selection via HSA was sequenced using Ion Torrent Personal Genome Sequencer (Life) following traditional protocols. Sequences were analyzed using in-house programs. Sequences were counted following orientation and rank ordering based on highest to lowest copy number. Families of sequences were grouped based on sequence similarity.

Example 3

Peptide Characterization Experiments

A. Cell Lines and Culture

The human pancreatic cell line HS766T were purchased from the American Type Tissue Collection (Manassas, Va.). HS766T were cultured in Dulbecco's modified Eagle medium (Life Technologies) with L-glutamine and 10% fetal bovine serum. HS766T were grown at 37° C. in a humidified atmosphere with 5% carbon dioxide.

B. Cell Proliferation Assay

A cell proliferation assay was performed using the BrdU Cell Proliferation Assay Kit (Cell Signaling Technology). Cells were seeded into 96-well plates at 1200 cells per well. Cells were treated with between 1 nM to 10 nM SUPR peptides generated against miRNA221 or 5 μM methotrexate (Fisher Scientific, Waltham, Mass.), as a control, and incubated at 37° C. with 5% $CO_2$ for 24 to 96 hr. After incubation 10 uL of the BrdU reagent was added with cell culture medium and incubated for 2 hr. Sample absorbance was analyzed using a microplate enzyme-linked immuno-absorbant assay reader at 490 nm. All experiments were performed at least in triplicate.

C. Confocal Experiments

Cells were seeded into black 96-well plates (Sigma-Aldrich) at 1200 cells per well. Cells were treated with 10 uM fluorescenated SUPR peptides generated against miRNA-221 and incubated overnight (ON). Images of the cells were taken with the EVOS Floid Cell Imaging Station (Life Technologies). The results are shown in FIGS. 8A-8D.

D. Digest

Human serum digest was performed against SUPR peptides generated against miRNA-221. 250 nmoles of peptides were suspended in 60 mg/mL Normal human serum (Pierce, Rockford, Ill.) and various time points were taken. Samples were run on reverse-phase high-performance liquid chromatography to analyze degradation of peptide. All experiments were performed at least in duplicate.

E. Fluorescence Polarimetry

Figure 3A:
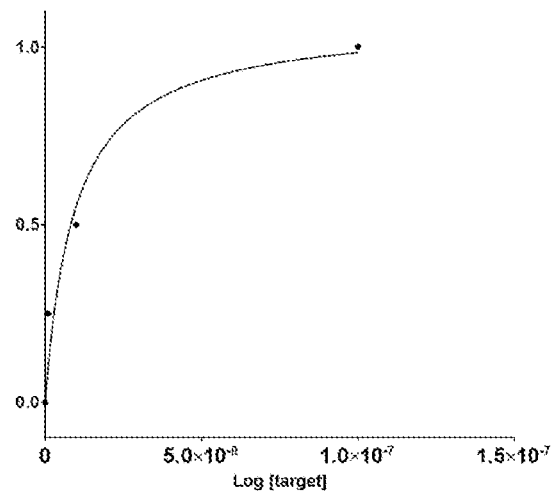
FIG. 3A is a graphic representation of the binding affinity of mR1.1 peptide, calculated by using the difference in anisotropy of the partially bound, free and fully bound states measured by titrating pre-miRNA-221.
Figure 3B:
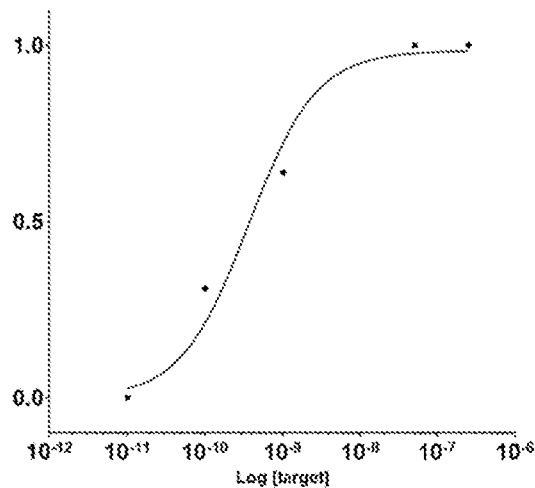
FIG. 3B is a graphic representation of the binding affinity of the MR3.1 peptide calculated by using the difference in anisotropy of the partially bound, free and fully bound states measured by titrating pre-miRNA-221 and peptide.

SUPR peptides generated against miRNA-221 were synthesized following traditional synthetic procedures with 5,6-FAM (AnaSpec, Fremont, Calif.). The target miRNA-221 was incubated with fluorescent peptides at 25 nM and read on a microplate reader (Synergy H4, BioTek, Winooski, Vt.). The degree of binding was calculated by using the difference in anisotropy of the partially bound, free and fully bound states measured by titrating miRNA-221 and peptide. The results are shown in FIGS. 3A-3B.

F. Affect on Protein Expression

Cellular lysate was extracted from H766T pancreatic cancer cells incubated with peptide for 48 hr. Total RNA was isolated from the lysate. An ampliseq panel of reverse primers (Life Technologies Grand Island, N.Y.) is used to reverse-transcribe and amplify target genes of interest. After an additional series of steps following the manufacturer's protocol, the amplified pool of genes is sequenced. Sequences are analyzed based on programs written by Life Technologies (Grand Island, N.Y.) which pool together like-genes and report total RNA expression levels.

Example 4

Affinity/Sequence Specificity of the Peptide

The affinity of the peptide for a specific target structure and its specificity for a particular sequence were analyzed by immobilizing the peptide on an SA sensor chip using a Biacore T200 (GE Healthcare, Boston, Mass.) using the manufacturer's protocols, and then measuring its affinity or specificity for the following RNA targets dissolved in HBST+EP buffer RT:

Pre-miR-221:
(SEQ ID NO: --)
ACAAUGUAGAUUUCUGUGUUCGUUAGGCAACAGCUACAUU with Point mutation 1:
(SEQ ID NO: --)
ACAAUUUAGAUUUCUGUGUUCGUUAGGCAACAGCUACAUU with Point mutation 2:
(SEQ ID NO: --)
ACAAUGUAGCUUUCUGUGUUCGUUAGGCAACAGCUACAUU with Point mutation 3:
(SEQ ID NO: --)
ACAAUGUAGAUUUCUUUGUUCGUUAGGCAACAGCUACAUU with Point mutation 4:
(SEQ ID NO: --)
ACAAUGUAGAUUUCUGUGUCCGUUAGGCAACAGCUACAUU with Point mutation 5:
(SEQ ID NO: --)
ACAAUGUAGAUUUCUGUGUUCGUUAGGCAACAUCUACAUU ssDNA:
(SEQ ID NO: --)
ACAATGTAGA TTTCTGTGTT CGTTAGGCAA CAGCTACATT dsDNA:
(SEQ ID NO: --)
ACAATGTAGATTTCTGTGTTCGTTAGGCAACAGCTACATT
annealed to its reverse complement Pre-miR-21:
(SEQ ID NO: --)
GACUGAUGUUGACUGUUGAAUCUCAUGGCAACACCAG Pre-miR-122:
(SEQ ID NO: --)
AUGGUGUUUGUGUCUAAACUAUCAAACGCCAU Pre-miR-222:
(SEQ ID NO: --)
AGUGUAGAUCCUGUCUUUCGUAAUCAGCAGCUACAUCU The results shown in FIGS. 6 and 7 demonstrate that the peptide is able to distinguish between different pre-miRNA sequences, binding only to pre-miRNA-221 and recognizing only the single-stranded pre-miRNA-221 structure.

EQUIVALENTS

Those skilled in the art will recognize, or be able to ascertain, using no more than routine experimentation, numerous equivalents to the specific composition and procedures described herein. Such equivalents are considered to be within the scope of this invention, and are covered by the following claims.

---

The invention claimed is:

1. A method of screening for a peptide which binds a preselected pre-miRNA and/or pri-miRNA, with at least nanomolar affinity, and which is at least partially protease-resistant, comprising the steps of:
   (a) preparing an mRNA library by transcribing a plurality of mRNAs from a plurality of synthetic DNAs with random base incorporation;
   (b) preparing a plurality of peptides by translation from the mRNA library in a translational system;
   (c) linking the resulting peptides to the mRNA encoding the peptides to form a plurality of peptide fusion products;
   (d) contacting the plurality of the peptide fusion products with a preselected pre-miRNA target and/or a preselected pre-miRNA target, the fusion products which are specific for the pre-miRNA target or pre-miRNA target binding to the target; and
   (e) isolating the peptide fusion products bound to the pre-miRNA and/or pre-miRNA targets.

2. The method of claim 1, wherein the contacting step is performed in the presence of a competitor RNA.

3. The method of claim 2, wherein the competitor RNA is tRNA.

4. The method of claim 1, wherein the isolating step comprises immunoprecipitating the peptide fusion products bound to the pre-miRNA target or to the pri-miRNA target.

5. The method of claim 1, further comprising selecting for the peptide fusion products which are membrane-permeable.

6. The method of claim 5, wherein the peptide fusion products are selected by Immobilized Artificial Membrane (IAM) High Performance Liquid Chromatography (HPLC).

7. The method of claim 1, further comprising subjecting the peptide fusion products to proteolysis with P450 enzymes, and selecting those peptide fusion products which are at least partially resistant to degradation.

8. The method of claim 1, wherein the preselected pre-miRNA and/or pre-miRNA is pre-miRNA-221 or pri-miRNA-221.

* * * * *